United States Patent [19]
Sauer et al.

[11] Patent Number: 4,828,418
[45] Date of Patent: May 9, 1989

[54] MOUTH HELD DEVICE

[76] Inventors: Barry W. Sauer, 500 Turtle Creek Dr.; Lyle D. Zardiackas, 12 Eastgate Ct., both of Brandon, Miss. 39042; Aaron D. Puckett, Jr., Rte. 1, Box 171, Jackson, Miss. 39212

[21] Appl. No.: 923,903

[22] Filed: Oct. 28, 1986

[51] Int. Cl.$^4$ .............................................. A46B 5/02
[52] U.S. Cl. .......................................... 401/6; 173/30; 414/9
[58] Field of Search .............. 433/71, 68, 34; 272/95; 128/136; 173/30; 401/6; 414/9; 224/181; 623/65

[56] References Cited

U.S. PATENT DOCUMENTS

| 316,636 | 4/1885 | Miles . | |
|---|---|---|---|
| 1,953,088 | 4/1934 | Purdy | 272/95 |
| 2,785,462 | 3/1957 | Barg | 401/6 |
| 3,251,909 | 5/1966 | Pickands et al. | 433/34 |
| 3,312,218 | 4/1967 | Jacobs | 128/136 |
| 3,411,501 | 11/1968 | Greenberg | 128/136 |
| 3,795,281 | 3/1974 | Cloran | 272/95 |
| 3,814,090 | 6/1974 | Hill | 128/145 A |
| 3,824,022 | 7/1974 | Mancino | 401/6 |
| 3,885,681 | 5/1975 | Mancino | 414/9 |
| 3,986,030 | 10/1976 | Teitscher | 250/349 |
| 4,218,167 | 8/1980 | Mansfield | 414/9 |
| 4,220,301 | 9/1980 | Jacobs et al. . | |
| 4,283,173 | 8/1981 | Browne | 433/34 |
| 4,472,140 | 9/1984 | Lustig | 433/71 |

FOREIGN PATENT DOCUMENTS

| 151137 | 9/1920 | United Kingdom | 272/95 |
|---|---|---|---|
| 172079 | 11/1921 | United Kingdom | 433/71 |

Primary Examiner—Richard J. Apley
Assistant Examiner—J. Welsh
Attorney, Agent, or Firm—Bacon & Thomas

[57] ABSTRACT

A mouth-held device is described that can be used by individuals having limited or no use of the hands. The device comprises a V-shaped plastic member having a shaft attached. The V-shaped plastic member must be able to soften at or near the boiling point of water and, at such softening point, to take an impression of the teeth of the individuals having limited or no use of the hands. When cooled to at or near body temperature, however, the V-shaped member must be rigid and non elastic and capable of retaining the impression of the teeth. The shaft attached to the V-shaped member can have various implements fixed to it that allows the individual having limited upper extremity function to perform certain tasks independently.

2 Claims, 1 Drawing Sheet

MOUTH HELD DEVICE

The present invention relates to an device held in the mouth and useful by individuals having limited or no use of their hands.

The device of this invention is designed to give a certain amount of independence to disabled individuals. The present invention provides for a low cost, conveniently custom formed, mouth controlled device that allows handicapped individuals to be more independent. Because of this independence, these individuals will rely less on attendants, thereby contributing to their emotional health.

The device of this invention is held in the mouth between the teeth, or gums in the edentulous individual. It is conventionally called a "mouth stick". In order to be most useful, the teeth must be firmly in contact with the portion of the device held in the mouth. The most advantageous prior art devices of this type are those that have the portion of the device held by the teeth custom molded by dental experts to the shape of the dental arch and occlusion of the teeth. As such, the resulting mouth stick is a rigidly held, very effective device of relatively high cost and inconvenience to the user. Further, because of the molding materials used, the custom made device is highly fragile, shattering easily. A mouth stick of this design is described by Blaine, et. al., J. Prosthet. Dent, 317, March 1973.

Accordingly, it is an object of this invention to provide a handicapped person with a degree of independence.

It is a further object of the present invention to provide a practical and convenient means of independence for those handicapped individuals who lack functional upper extremity movement.

It is another object of the present invention to provide a device conveniently custom formed to the shape of the teeth and held in the mouth that allows the handicapped to perform certain activities without the help of attendants.

These and other objects of the present invention will be apparent from the following figures and description and appended claims.

Figure 1:
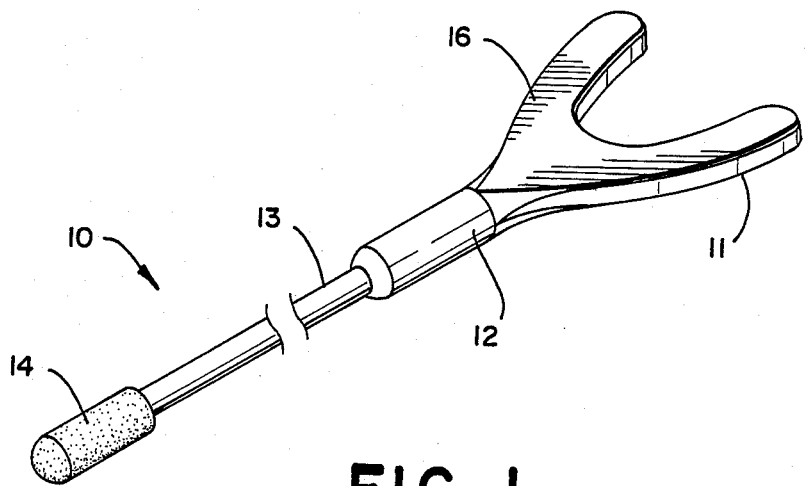
FIG. 1 represents a perspective view of the device of the present invention.

Referring now to FIG. 1, the mouthstick 10 consists of a single V-shaped member 11 made from a material which may be molded at a temperature higher than body temperature but lower than that which will burn mouth tissues, to conform to the wearer's teeth, and which, after cooling, is tough, durable and shape-retaining at body temperature. It is of particular importance that the mouthpiece material should not soften or otherwise lose any of its hardness at body temperatures, since the mouthpiece will be substantially at body temperature during all periods of use. The material should also be adapted to receive a new impression of the teeth upon being reheated to a temperature above body temperature. The mouthpiece member 11 is a plastic material of high molecular weight. It has a vicat temperature of about 57°–79° C. (ASTM D-1525-70, Rate B) and a melting point of about 81°–95° C. Because it must be shape retaining and non elastic at or near body temperature, its flexural modulus is between 100 and 380 megapascals (ASTM D-790). One such preferred material is a resin comprising an methacrylic acid ethylene copolymer, which is sold by DuPont under the trade name SURLYN. In particular, the material identified by DuPont as SURLYN 8000 and 9000 has been found to be especially well suited for this invention. These thermoplastic copolymers are odorless, tasteless and carry Federal Food and Drug Administration approval for use as food packaging materials. Typically, they are unfilled. However, in some cases, a filler may be desired to alter processability or provide odor. Such fillers, also, require Food and Drug Administration approval.

It is important that the material selected for the V-shaped member and attachment part 12 should have adequate rigidity to prevent deformation at body temperature since control of the shaft 13 and tip 14 are adversely affected by soft and resilient materials.

The mouthpiece 11 is a substantially flat, V-shaped member having a substantially stiff shaft secured to it through attachment part 12. Part 12 is preferably molded into the mouthpiece 11 and is in the shape of a hollow cylinder adapted to receive a solid or hollow cylindrical shaft 13. See FIG. 2. However, it should be understood that other shapes for shaft 13 and part 12 can also be used, e.g., oblong, square, etc. Shaft 13 terminates with tip 14, typically of a soft rubbery material useful for turning pages and the like. However, other implements can be attached in place of tip 14, e.g., a pen, pencil, brush and the like.

The V-shaped member 11 can be molded according to the preferred method to receive an impression conforming to the shape of the teeth (including false teeth or the gums where no teeth are present) of the wearer in a matter of seconds. This method is easily employed by the user of the mouthpiece, and an able bodied assistant. No special equipment is required to secure a good fit. The first step of the method is to heat the member 11 to a temperature higher than body temperature and sufficient to cause the plastic material to soften and become moldable under moderate pressure. For the preferred material identified above, the minimum temperature at which the mouthpiece may be readily molded is approximately 70° C. Heating of the mouthpiece member 11 is most efficiently accomplished by placing it in boiling water for a length of time sufficient to raise the temperature of the mouthpiece member 11 to the desired level. The length of time that the member is in the boiling water may typically range from about 2 to 5 minutes, 3 minutes normally being sufficient to raise the temperature of the member to between approximately 70° C. and 80° C., the optimum temperature range for molding the mouthpiece in the mouth. While a member of the preferred material may be readily molded at temperatures up to 200° F., it should not be heated to a temperature so high that it will burn the soft tissue of the mouth when inserted therein, if it is to be molded within the mouth to conform to the bite of the user according to this preferred method. The presence of a liquid film on the surface of the member 11 when it is removed from the boiling water will cool the surface slightly by evaporation, and there will be less discomfort to the mouth tissue than if the member is heated by dry air to the same temperature. However, a brief immersion (three to five seconds) in cold tap water will also serve to cool the surface sufficiently to prevent tissue injury.

Figure 2:
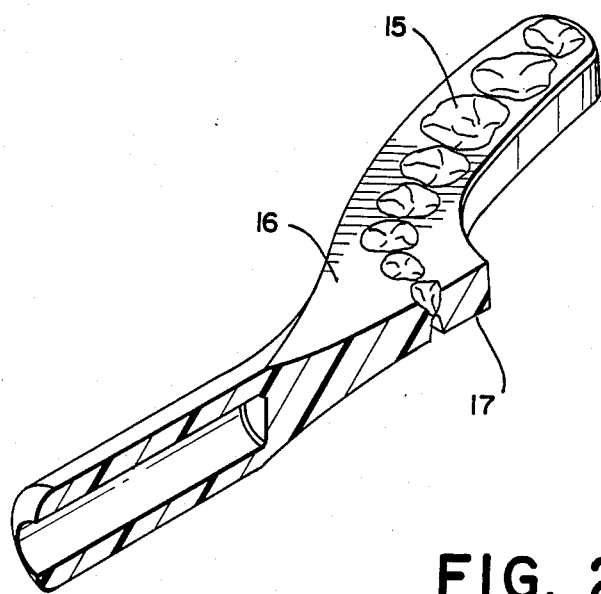
FIG. 2 represents a cross-sectional view of the V-shaped member 11 of FIG. 1.

After it has been immersed in the boiling water a sufficient length of time to raise its temperature to the desired level, member 11 is removed by shaft member 13, typically briefly cooled and placed in the mouth between the upper and lower teeth. If the member has been overheated, it should be allowed to cool slightly until it can be placed in the mouth without causing discomfort or burning. The user then bites down on the mouthpiece member 11 with a force sufficient to impress the shape of the individual teeth in the cooling, but still soft, plastic material. The teeth imbed themselves in the softened material (0.5–5 mm) leaving an impression. The mouthstick 10 may then be removed and member 11 further cooled, preferably by placing in cold water or under a cold water tap, to harden the mouthpiece member so that it will retain the impression. The mouthstick 10 will then be custom fit to the teeth of the wearer. As shown in FIG. 2, the surface 16 of the top and the surface 17 of the bottom, will bear a distinct impression 15 of the wearer's teeth. This impression will last indefinitely during usage until the mouthpiece is again heated to a temperature above body temperature at which time it is easily remolded. If, through faulty technique, a satisfactory fit is not obtained, or the fit becomes loose after extended usage, the mouthpiece member 11 of mouthstick 10 may be re-fitted to the wearer's teeth. This is done by simply repeating the procedure involved in making the first impression. The entire procedure takes only minutes to complete.

The physical limitations and capabilities of the individuals needing to use the mouthstick necessarily vary widely. It should be noted that angular adjustments of shaft 13 relative V-shaped member 11 can also be easily accomplished. Once softened by heating, the shaft 13 can be easily moved from side to side and up or down, i.e., attachment part 12 becomes flexible. On cooling, the repositioned shaft remains in place until the user desires to change such position again. Further repositioning is possible simply by repeating the softening procedure. The repositioning is advantageously accomplished when the V-shaped member 11 is held firmly between the teeth. It will thus be seen that the objects set forth above among those made apparent from the preceding description and drawings, are efficiently attained and, since certain changes may be made in the above construction without departing from the spirit and scope of the invention, it is intended that all matter contained in the above description as shown in the accompanying drawings shall be interpreted as illustrative and not in a limiting sense.

I claim:

1. A mouth-held device for permitting a person with limited or no use of the hands to independently perform certain tasks or activities, which device comprises:
    (a) a substantially V-shaped plastic member including an integrally formed socket and formed of a material that is softenable at or near the boiling point of water for the purpose of taking impressions of the teeth of the person, but remaining rigid and nontractable when at or near body temperature;
    (b) a shaft having one end secured within the socket, whereby when the plastic member is softened, the angular position of the shaft relative to the plastic member may be varied; and
    (c) the other end of the shaft being configured for attachment to an implement for performing a given task or activity when the plastic member is held in the mouth of the person.

2. The mouth-held device of claim 1 wherein the material forming the plastic member is a thermoplastic copolymer having a melting point of about 81°–96° C., Vicat temperature of about 57°–79° C., and a flexural modulus of about 100–380 mpa, the copolymer being capable of taking an impression when at or above the softening point and retaining the impression when at or near body temperature.

* * * * *